United States Patent [19]

Wada et al.

[11] Patent Number: 5,501,956

[45] Date of Patent: * Mar. 26, 1996

[54] POLYREDOX COUPLES IN ANALYTE DETERMINATIONS

[75] Inventors: Henry G. Wada, Atherton; Harden M. McConnell, Stanford; Dean G. Hafeman, Hillsborough, all of Calif.

[73] Assignee: Molecular Devices Corporation, Sunnyvale, Calif.

[*] Notice: The portion of the term of this patent subsequent to Jul. 17, 2007, has been disclaimed.

[21] Appl. No.: 185,730

[22] Filed: Jan. 24, 1994

Related U.S. Application Data

[63] Continuation of Ser. No. 952,465, Sep. 28, 1992, abandoned, which is a continuation of Ser. No. 497,988, Mar. 23, 1990, abandoned.

[51] Int. Cl.[6] .............................. C12Q 1/60; G01N 27/26
[52] U.S. Cl. ................... 435/11; 435/14; 435/18; 435/817; 204/403; 205/777.5
[58] Field of Search ................. 435/7.95, 11, 18, 435/21, 25, 14, 28, 817; 204/153.12, 403

[56] References Cited

U.S. PATENT DOCUMENTS

| | | | |
|---|---|---|---|
| 4,385,114 | 5/1983 | Guthlein | 435/28 |
| 4,591,550 | 5/1986 | Hafeman | 435/4 |
| 4,942,127 | 7/1990 | Wada | 435/11 |

*Primary Examiner*—Ralph J. Gitomer
*Attorney, Agent, or Firm*—Banner & Allegretti, Ltd.

[57] ABSTRACT

Enzyme or substrate determinations can be achieved by employing an organic second substrate, which produces a product which may be coupled with a metal inorganic redox couple capable of interacting with and affecting the potential of a metal electrode on a semiconductor surface. Particularly, hydrogen peroxide or indoxyl phosphate are coupled with iron- or ruthenium-containing ionic redox couples for determination with a noble metal electrode.

17 Claims, No Drawings

POLYREDOX COUPLES IN ANALYTE DETERMINATIONS

This is a continuation of application Ser. No. 07/952,465 filed Sep. 28, 1992, now abandoned which is a continuation of application Ser. No. 07/497,988, filed Mar. 23, 1990 now abandoned.

TECHNICAL FIELD

The field of this invention is the use of biosensors to detect redox reactions involving enzymes.

BACKGROUND

For the most part, assays involving the detection of enzyme activity, either for measuring enzyme substrate, enzyme, or the enzyme as a label have depended upon colorometric or fluorimetric detection. However, there has been a continuous and expanding interest in electrical detection using either amperometric or potentiometric methods. These methods require a redox couple which can be detected at an electrode.

There are many constraints in developing a diagnostic system. Compositions must be developed which allow for the transport of electrons from the enzyme or a product of the enzyme. The various materials which are employed must not interfere with each other, so that neither the enzyme reaction, nor the transfer of electrons to the electrode, are adversely affected. Because in many instances the analyte is present in very low concentration, it is important that the individual reaction related to the amount of analyte be very rapid, desirably diffusion controlled. In this circumstance, there will be a rapid response for each enzymatic event.

It is therefore of interest to devise compositions which may be used in the electrical detection of enzymatic reactions, by providing for rapid and efficient transfer of electrons to an electrical sensor as a result of enzymatic reaction.

RELEVANT LITERATURE

Frew and Mill, *Anal. Chem.* (1987) 59:933A 944A, provide a review of electrochemical biosensors. Josephy et al., *J. Biol. Chem.* (1982) 257:3669–3675 describe the use of tetramethylbenzidine as a horse radish peroxidase substrate. References of interest employing biosensors in enzyme immunoassays include Heineman et al., *Anal. Proc.* (1987) 24:324–325; Alwis and Wilson, *Anal. Chem.* (1987) 59:2786–2789; Gyss and Boutdillon, *Anal. Chem.* (1987) 59:2350–2355; Sayo et al., *J. of Chromat.* (1987) 417:129–134; Lunte et al., "Immunoassay by HPLC and Flow Injection Analysis with Electrochemical Detection" In *Proceedings of the Symposium on Electrochemical Sensors for Biomedical Applications*, ed. Li, Vol. 86–14, Electrochemical Soc., Inc., N.J., 1986, pp. 129–138; Wehmeyer et al., *Anal. Chem.* (1986) 58:135–139; Janata, *Anal. Proc.* (1987) 24:326–328; Weetall and Hotaling, *Biosensors* (1987) 3:57–63; Davis, Biosensors (1986) 2:101–124; and EPA 85/114836.3.

SUMMARY OF THE INVENTION

Compositions are provided for determining enzymatic activity in a medium employing an organic substrate coupled with an inorganic redox couple for efficient transfer to a metal electrode.

DESCRIPTION OF THE SPECIFIC EMBODIMENTS

Methods and compositions are provided for detecting enzymatic reactions employing a metal electrode. The methods employ a combination of reagents, where the first reagent provides for a rapid efficient reaction with the enzyme to produce a product capable of reacting with the second reagent, where the second reagent may be determined amperometrically or potentiometrically. The method may involve direct detection of the enzyme, use of an enzyme as a label for detection of ligands, or use of an enzyme to detect enzyme substrate.

The enzymes to be detected are hydrolases, particularly phosphatases, or oxidoreductases, particularly peroxidases, which may be used by themselves or in conjunction with oxidases. The oxidases can produce a product, particularly hydrogen peroxide, with which the peroxidase may react to produce another product which reacts with the second reagent. Oxidases which may be coupled with the peroxidase include glucose oxidase, xanthine oxidase, uricase, cholesterol oxidase, and the like.

The hydrolases, particularly esterases or saccharidases, such as β-galactosidase, can provide hydrolysis of indoxyl esters,-where the acid group may be organic or inorganic, including carboxylates, phosphates, sulfates, etc., or indoxyl glycosidyl ethers, such as β-galactosidyl, β-glucosidyl, etc.

The second reagent is an inorganic redox couple, normally employing an iron or ruthenium couple. The iron may be in any convenient form, particularly coordinated, such as with hexacyanoferrate, e.g. ferroor ferricyanide, ferrocene, or other stable form of iron, capable of undergoing one electron transfer. The ruthenium will also be coordinated with a variety of ligands, particularly nitrogen ligands, such as pyridine, substituted pyridines, bis-pyridines, pyridine, amino, substituted amino, or the like. The ruthenium preferably will be employed in the divalent state, coordinated with 5 $NH_3$ ligands and 1 pyridine ligand.

Various metal electrodes may be employed, particularly inert or noble metal electrodes, such as gold, rhodium, platinum, etc. As will be discussed, the metal electrode may be used in relation to the semiconductor electrode as is described in application Ser. No. 072,168, filed Jul. 10, 1987, which disclosure is incorporated herein by reference.

The first reagent will be selected so as to be able to react rapidly and efficiently with the enzyme to produce a product which will have an electromotive potential so as to be capable of reacting with the second reagent. Thus, the first and second reagents are related in that the electromotive potential of the product of the enzymatic reaction must be at a higher potential than the electromotive potential for the inorganic redox couple.

For use with peroxidases, benzidine or benzidine derivatives can be employed as the first reagent with advantage, where the benzidine will usually be not more than about 30 carbon atoms, usually not more than about 20 carbon atoms, and may have from 0 to 4, usually from 0 to 2 other heteroatoms as substituents, where the heteroatoms will usually be oxygen or nitrogen, normally present as oxy, oxo or amino, where the oxygen and nitrogen may be substituted with hydrogen or alkyl of from 1 to 3, usually from 1 to 2 carbon atoms. Generally, there will not be more than 4 substituents bonded to annular carbon atoms, usually not more than 2 substituents bonded to annular carbon atoms, other than the amino groups of the benzidine. Illustrative substituents include methyl, ethyl, hydroxyl, methoxy, methylamino, etc.

Indoxyl esters will have the ester group at the 3 position and may be otherwise substituted or unsubstituted, usually unsubstituted, where substituents may be alkyl of from 1 to 3 carbon atoms, oxy of from 0 to 3 carbon atoms, amino of from 0 to 3 carbon atoms, or halogen, where the ethers and substituted amino groups will be substituted by alkyl of from 1 to 3 carbon atoms, usually of from 1 to 2 carbon atoms. Halogen substituents may be chlorine, fluorine, or bromine groups, usually 1 to 3, and preferably 2 groups, per indoxyl molecule. As indicated previously, a variety of esters may be employed, which include phosphate, acetate, lactate, sulfate, or the like, or glycosidyl ethers.

Depending upon the purpose of the reaction, various protocols will be employed, as well as various concentrations. For directly measuring an enzyme, the enzyme concentration may be varied widely, depending upon the sample. Usually, the enzyme will be present in from about 0 to 1 µg, more usually from about 0 to 10 ng. In addition, this will vary depending upon whether a peroxidase or hydrolase is involved, with the peroxidase being from about 0.1 pg to 10 ng, while the hydrolase will generally be from about 1 pg to 100 ng.

The benzidine compound will usually be present in about 50 µM to 1 mM, more usually in 100 to 400 µM. The amount of benzidine will be selected so as to be non-rate limiting, so as to provide substantially a $V_{max}$. The indoxyl compound will also be present in non-limiting amounts generally being present in 0.1 to 2 mM.

The inorganic redox couple generally will be at a concentration in the range of about 1.0 to 1000 µM, more usually from about 10 to 200 µM.

The solution will be buffered to optimize substantially the enzymatic activity, generally having a pH in the range of about 4 to 12, more usually from about 5.5 to 10 depending upon the pH optimum of the enzyme with the substrates employed. Various buffers may be employed, which include tris-(hydroxymethyl) methylamine (Tris), phosphate, borate, or the like, usually employing a buffer suitable for the particular enzyme system.

For measuring the enzyme, the various components may be brought together in an appropriately buffered medium in contact with the metal electrode and the rate of change of redox potential in the medium determined.

Where the enzyme is a label, a wide variety of protocols are available. Various assay compositions are commercially available, involving heterogeneous protocols (a separation step) or homogeneous protocols (no separation step). Assay kits are sold which are generally referred to as ELISA or under the trademark EMIT. In performing an ELISA, the medium containing the enzyme conjugate is separated from the enzyme conjugate which has become bound to a support. Modulation of binding of enzyme conjugate is due to a competition between a complementary specific binding pair member bound to a support, and an analyte in solution. Alternatively, in a sandwich assay, the analyte acts as a bridge between a complementary specific binding pair member, which is attached to the support, and the enzyme conjugate. Thereby, the analyte also modulates the binding of enzyme conjugate. Various protocols have appeared in the patent literature and may be exemplified by such patents as U.S. Pat. No. 4,376,110.

For homogeneous enzyme immunoassays, the various reagents may be brought together, where binding of the complementary specific binding pair member to the enzyme conjugate results in a change in enzymatic activity. Thus, in this instance, one need not separate the bound from free enzyme conjugate.

In the heterogeneous assay, the subject reagents may be added to either the surface bound enzyme or to the separated supernatant for determination of enzymatic activity. Enzymatic activity is then monitored with a metal electrode in accordance with the subject invention.

Illustrative of the subject method is the determination of cholesterol, where the cholesterol may be present in a variety of forms, such as HDL, LDL, VLDL or uncomplexed. The cholesterol serves as a substrate for cholesterol oxidase to form hydrogen peroxide, which acts as a substrate for horseradish peroxidase.

The metal electrode may be any type of metal electrode, wire, wafer, grid, or the like. Of particular interest in the subject invention is the use of a metal electrode which is in electrostatic proximity contact with a semiconductor. This device is described in U.S. application Ser. No. 072,196, filed Jul. 10, 1987, whose disclosure is incorporated herein by reference. The apparatus of U.S. Pat. No. 4,591,550 also may be used where such device is modified by affixing to the insulating surface a thin metal film to serve as the metal electrode, so that a plurality of assays may be carried out, where each of the metal electrodes bound to the insulating surface are insulated one from the other. Any means of insulation may be used such as, separating the sample solutions associated with each of the metal electrodes with dividers or using gelled samples which are insulated one from the other, or the like.

The metal electrode will be present on an insulating layer, e.g. silicon oxide or silicon oxynitride with silicon, of about 0.1 to 10 mm thickness. The metal electrode will generally have a surface area of about 0.1 to 5 mm$^2$ and about 0.1 to 1000 µ thickness. The electrode may be electrodeposited or affixed with an adhesive which is stable under the conditions to which it is subjected. For example, the electrode may be 0.5 µ of gold over 300 Angstroms of chromium over 1000 Angstroms of silicon nitride over 300 Angstroms of silicon oxide over n-type silicon. Any surface of the semiconductor which is exposed to the medium will be protected with an insulating coat, e.g. 1000 Angstroms silicon nitride over 100 Angstroms of silicon oxide.

The following examples are offered by way of illustration and not by way of limitation.

EXPERIMENTAL

EXAMPLE 1

Detection of Horseradish Peroxidase

The apparatus employed is described in European patent application Ser. No. 87.305456.3, filed Jun. 19, 1987. The particular construction employed for the following tests is as follows:

The gold layer of about 4.2 mm diameter was placed on a 2.5 mm×5.0 mm rectangular silicon chip which is positioned in a reading chamber containing a platinum controlling electrode and an Ag/AgCl reference electrode. A membrane with the enzyme of interest bound to it or included in it is positioned over the gold electrode and a plastic plunger is pressed against the membrane to restrict diffusion of reagents from the localized environment of the membrane.

The silicon chip is fabricated from a 4-inch diameter wafer of N <100> silicon of approximately 10 to 15 ohm-cm resistivity. The insulator is composed of approximately 340 Angstroms of silicon oxide adjacent to the silicon and overlaid with 1000 Angstroms of silicon nitride deposited by chemical vapor deposition from a reaction of dichlorosilane and ammonia at about 800° C. in a low pressure chamber. The wafers are subsequently annealed in a hydrogen ambient at 1050° C. for 1 hour. The ohmic contact to the silicon chip is made by evaporating approximately 0.5 μ of gold—1% arsenic onto the (bare) etched back surface of a silicon wafer, etching away the gold from regions where light penetration is desired and then alloying the gold into the silicon at 450° C. The sensing gold layer next is deposited over the silicon nitride insulating layer by evaporation in a low pressure chamber of first 300 Angstroms of chromium followed by 5000 Angstroms of gold. The 4.2 mm circles are then formed by protection with a positive photoresist followed by etching first the gold and then the chromium by means of standard metal-etching techniques.

The following reagents were employed:
1) horseradish peroxidase;
2) tetramethylbenzidine (TMB) (20 mg/ml in 95% ethanol);
3) peroxidase buffer: 0.1 M NaAcetate, 1 mM EDTA, 7.5% ethanol, pH 5.5;
4) potassium retro- or ferricyanide, each 100 mM in water.
5) Ruthenium Pentaamine Pyridine Perchlorate, 4.4 mM in water.

A redox solution was-prepared comprising TMB 200 μM, Ruthenium $^{+2}$ pentaamine pyridine 25 μM, $H_2O_2$, 250 μM, in peroxidase buffer. Concentrations of horseradish peroxidase on a nitrocellulose support were introduced into the chamber and readings taken by employing a sweep −0.5 to −1.5 volts, gain 16, sweep time 0.4 sec. At 800 pg HRP, the observed result was −3046 μV/s, at 91 pg, −1784 μV/s, at 6 pg, and −327 μV/s at 0 ng. It is evident that by employing the benzidine substrate, TMB, and an inorganic redox couple, ruthenium pentamine pyridine, it is possible to rapidly detect (within 60 secs) −1 pg of HRP, $2.5 \times 10^{-17}$ moles of HRP, or $16 \times 10^6$ molecules of HRP.

In the next study, detection of microorganisms was demonstrated. A solution was prepared of N. meningitidis ($4 \times 10^9$ cells/ml). A monoclonal antibody-HRP conjugate was prepared and employed in 1:200 dilution in 40% fetal bovine serum (FBS). The membrane filter (polycarbonate) had a 0.2 μm pore 0.2 ml of sample containing varying concentrations of cells was filtered onto the filter followed by incubation with 50 μl of conjugate, after which time the filter was washed 2× with PBS and 1× with NaCl (0.9%)-Tween-20 (0.05%). To the substrate buffer (0.1 M NaAc, 1 mM EDTA, 5% ethanol, pH 5.5, 0.1% Triton X-100) was added: TMB (200 μM); ferrocyanide (100 μM); and hydrogen peroxide (250 μM). Following the procedure described above, the signal was determined for $8 \times 10^3$, $8 \times 10^4$ and $8 \times 10^5$ cells. The observed signal for $8 \times 10^3$ cells was 4.6× the negative signal (−80 μV/s) −369 μV/s, the $8 \times 10^4$ cells' signal was −2231, and the $8 \times 10^5$ cells signal was −10080.

When ferrocene was employed in place of the ferrocyanide at a concentration of 200 μM and $8 \times 10^3$ cells, the ratio was 3.5× neg, while with 800 cells, the ratio was 1.36× neg.

In the next study, ferri-/ferrocyanide was used as the inorganic redox pair in conjunction with TMB.

The reaction solution was 10 μM in potassium ferrocyanide, 0.1 M NaAcetate, pH 5.5, 1 mM EDTA, 0.1% Triton X-100, 5% ethanol, 250 μM hydrogen peroxide, 200 μM TMB.. The HRP conjugate (Lot No. 7-6-87A) was diluted 1:200 in 40% FBS and a N. meningitidis medium ($4 \times 10^9$ cells/ml in PBS-Tween-20) was employed. The cell medium (0.2 ml) was filtered through a 0.2 μm pore polycarbonate membrane, followed by contacting the membrane for 10 min with 50 μl of the conjugate, followed by washing once with PBS and once with water. The membrane was then introduced into the measuring compartment. At 800 cells/ml, the observed voltage change (−210 μV/s) was 2.2× negative (−94), and at 8000 cells/ml (−936), 10× negative. Thus, ferrocyanide can be used in a sensitive method for detection of organisms through a redox couple.

In the next study, a Genetran membrane was employed and the analyte was a nucleic acid sample. Genetran is a positively-charged nylon membrane. The membrane was washed using 5% Triton in PBS, pH 7.0, 4×200 μl. Heat denatured single-stranded calf thymus DNA in deionized water (50 μl) was added to the membrane. SSB-HRP conjugate solution (single-stranded DNA binding protein was coupled using maleimide crosslinking chemistry to thiolated HRP) was diluted 1:15,000 in 0.2% BSA, PBS, 0.05% Tween-20, and 300 μl of the solution perfused through the membrane using a peristaltic pump, the filtration requiring 3–4 min. The membrane was then washed 3×200 μl with 5% Triton X-100 in PBS, followed by 3× 200 μl in peroxidase buffer. The membrane was then introduced into a compartment which contained the substrate solution comprising 25 μM of $Ru^{+2}$ chelate (same as previous example), 200 μM TMB, and 250 μM hydrogen peroxide in the previously described buffer. In the absence of DNA, the voltage change was +262 μV/s, while at 150 pg, the voltage change was −63, at 600 pg, −2474, and at 2500 pg, −16000. In a repeat of the determination, the negative control gave a voltage change of 150 μV/s, at +150 pg DNA, −312, at 600 pg DNA, −3116, and at 2500 pg DNA, −19268.

EXAMPLE 2

Detection of Alkaline Phosphatase

The apparatus employed was a redox sensor, which used a gold spot on silicon water for the metal electrode as described in Example 1. The following reagents were employed:
1) Calf intestinal Alkaline Phosphatase
2) BCIP (5-Bromo-4-chloro-3-indolylphosphate, toluidine salt)
3) Alkaline phosphatase Buffer:
0.2 M Tris (Tris-[hydroxymethyl]aminomethane)
1 mM $MgCl_2$, 0.05% $NaN_3$, 0.1% Tween 20, pH 10.0

The assay was based on using alkaline phosphotase as the enzyme, and the hydrolysis of indoxyl phosphate to indoxal. Indoxal is coupled to the inorganic redox component to generate a potentiometric signal.

The procedure employed was to add 10 μl of alkaline phosphatase solution or buffer to 1 ml of substrate containing 1 mM indoxyl phosphate, 1 mM ferricyanide and 0.5 mM ferrocyanide in 0.2 M Tris buffer, 1 mM magnesium acetate, 0.05% sodium azide, pH 10.3. This solution was quickly mixed and added to the measurement compartment. Measurements were made every 0.18 min.

The buffer alone gave a +6.6 μV/s rate. The addition of BSA carrier protein (2%) further increased the background rate to +16 μV/s. Increasing amounts of enzyme were added to the measuring compartment, starting at 7.8 ng/ml as the-concentration in the cell and increasing to 124 ng/ml. The reaction rate, change in potential (μV/s) voltage, was linear in the first 2 minutes of measurement. The reaction rate accelerated as the ferricyanide was consumed, which occurred at the two highest enzyme levels tested, 124 and 250 ng/ml. The reaction rate was proportional to enzyme concentration from 7.8 to 250 ng/ml, a linear regression analysis gave a $R^2$ value of 0.997. An estimate of the sensitivity of the method was conservatively placed at 10 ng/ml. Reduction of the volume of the reaction cell to 0.1 μl should increase the sensitivity to 1 pg of alkaline phosphatase. This represents $8.3 \times 10^{-18}$ moles of alkaline phosphatase or approximately $5 \times 10^6$ molecules.

It is evident from the above results, that by using an organic molecule capable of being a substrate for an enzyme and capable of interacting with a metallic redox pair, which in turn can affect the potential of a metal electrode on a semiconductor surface, great sensitivity can be achieved. In particular, hydrogen peroxide and TMB or indoxyl phosphate may be used in conjunction with ferri- ferrocyanide or ruthenium chelates to couple alkaline phosphatase and peroxidase to a metal electrode. These enzymes may be used as labels or in conjunction with other enzymes to measure the presence of specific analytes. Thus, highly sensitive assays for determining a wide variety of analytes and enzymes are obtained which may be carried out rapidly, accurately, with high sensitivity and in very small volumes.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. In a method for determining the presence of an oxidase in an assay medium by employing a metal electrode for detection of a redox reaction, the improvement which comprises:

(a) a tetramethylbenzidine and hydrogen peroxide; with (b) an iron or ruthenium containing ionic redox couple in the assay medium.

2. A method according to claim 1, wherein said oxidase is horseradish peroxidase and said hydrogen peroxide is produced in said assay medium by the enzymatic reaction of said oxidase with a substrate for the oxidase in said assay medium.

3. A method according to claim 1, wherein said oxidase is horseradish peroxidase and said hydrogen peroxide is produced in the assay medium by a reaction of cholesterol oxidase or glucose oxidase with a substrate for the oxidase.

4. A method according to claim 1, wherein said iron containing ionic redox couple is hexacyanoferrate redox couple.

5. A method according to claim 1, wherein said ruthenium containing ionic redox couple is ruthenium pentamine complex.

6. In a method for determining the presence of peroxidase in an assay medium by employing a metal electrode for detection of a redox reaction, the improvement which comprises:

(a) a benzidine and hydrogen peroxide; with (b) an ionic redox couple containing an element selected from the group consisting of iron and ruthenium in the assay medium.

7. A method according to claim 6, wherein the metal is a noble metal.

8. A method according to claim 6, wherein the hydrogen peroxide is produced in the assay medium by an enzymatic reaction in the assay medium.

9. In a method for determining the presence of an oxidase in an assay medium by employing a metal electrode for detection of a redox reaction, the improvement which comprises:

(a) a tetramethylbenzidine and hydrogen peroxide, with (b) an ionic redox couple containing an element selected from the group consisting of iron and ruthenium in the assay medium.

10. A method according to claim 9, wherein the oxidase is horseradish peroxidase and the hydrogen peroxide is produced in the assay medium by an enzymatic reaction in the assay medium during the assay.

11. A method according to claim 9, wherein the oxidase is horseradish peroxidase and the hydrogen peroxide is produced in the assay medium by a reaction of cholesterol oxidase or glucose oxidase with a substrate for the oxidase.

12. A method according to claim 9, wherein the ionic redox couple containing iron is a hexacyanoferrate redox couple.

13. A method according to claim 9, wherein the ionic redox couple containing ruthenium is a ruthenium pentamine pyridine redox couple.

14. In a method for determining the presence of a hydrolase in an assay medium by employing a metal electrode for detection of a redox reaction, the improvement which comprises:

(a) a compound selected from the group consisting of indoxyl ester and other; with (b) an ionic redox couple containing an element selected from the group consisting of iron and ruthenium in the assay medium.

15. A method according to claim 14, wherein the ionic redox couple containing ruthenium is ruthenium pentamine pyridine redox couple.

16. A method according to claim 14, wherein the ionic redox couple containing iron is a hexacyanoferrate redox couple.

17. A method according to claim 14, wherein the hydrolase is alkaline phosphatase and the indoxyl ester is indoxyl phosphate.

\* \* \* \* \*